United States Patent [19]

Rizzardo et al.

[11] Patent Number: 6,034,263

[45] Date of Patent: *Mar. 7, 2000

[54] CONTROL OF MOLECULAR WEIGHT AND END GROUP FUNCTIONALITY IN POLYMERS USING UNSATURATED PEROXY COMPOUNDS AS CHAIN TRANSFER AGENTS

[75] Inventors: Ezio Rizzardo, Wheelers Hill; Gordon Francis Meijs, Murrumbeena; San Hoa Thang, Clayton South, all of Australia

[73] Assignee: Commonwealth Scientific and Industrial Research Organisation, Australian Limestone Territory, Australia

[*] Notice: This patent issued on a continued prosecution application filed under 37 CFR 1.53(d), and is subject to the twenty year patent term provisions of 35 U.S.C. 154(a)(2).

[21] Appl. No.: 08/468,305

[22] Filed: Jun. 6, 1995

Related U.S. Application Data

[62] Continuation of application No. 08/202,473, Feb. 28, 1994, Pat. No. 5,698,648, which is a continuation of application No. 08/060,503, May 12, 1993, abandoned, which is a continuation of application No. 07/849,088, filed as application No. PCT/AU90/00523, Oct. 30, 1990, abandoned.

[51] Int. Cl.[7] .................................................. C07C 409/00
[52] U.S. Cl. .......................... 558/387; 560/205; 568/568; 526/232; 526/232.5
[58] Field of Search ............................... 526/232, 232.5; 568/568; 558/387; 560/205

[56] References Cited

PUBLICATIONS

Waldemar Adam and Axel Griesbeck, Synthesis pp. 1050–1052, 1986.

*Primary Examiner*—Bernard Lipman
*Attorney, Agent, or Firm*—Bacon & Thomas

[57] ABSTRACT

A process for the production of lower molecular weight polymers by free radical polymerization, characterized in that there is added to the polymerization system a compound of the general formula I

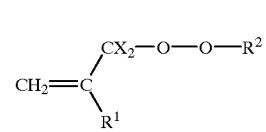

wherein $R^1$ is hydrogen, chlorine, an alkyl group, or a group capable of activating the vinylic carbon towards free radical addition;

$R^2$ is hydrogen or an optionally substituted alkyl, alkenyl, aryl, cycloalkenyl or cycloalkyl group or the group —COZ, where Z is $R^3$ or $OR^3$, where $R^3$ is hydrogen or an optionally substituted alkyl, alkenyl or aryl group.

X is a hydrogen atom, an alkyl or aryl group, or a halogen, and the two X groups may be the same or different.

The invention also includes polymers or oligomers made by the process and novel compounds of the generated formula I as defined above.

6 Claims, No Drawings

CONTROL OF MOLECULAR WEIGHT AND END GROUP FUNCTIONALITY IN POLYMERS USING UNSATURATED PEROXY COMPOUNDS AS CHAIN TRANSFER AGENTS

This application is a Continuation of application Ser. No. 08/202,473, filed Feb. 28, 1994, now U.S. Pat. No. 5,698,648, which is a Continuation of application Ser. No. 08/060,503, filed May 12, 1993, now abandoned, which is a Continuation of application Ser. No. 07/849,088, filed May 20, 1992, now abandoned, filed as PCT/AU90/00523, filed Oct. 30, 1990, now abandoned.

This invention relates to processes for radical-initiated polymerization of unsaturated species and for the control of molecular weight of the polymeric products produced from such processes. Polymers of limited molecular weights, or oligomers, are useful as precursors in the manufacture of other polymeric materials and as additives or components of formulations for plastics, elastomerics, and surface coating compositions, as well as being useful in their own right in many applications.

The manufacture of low molecular weight polymers normally requires the use of both an initiator, which acts as a free radical source, and a chain transfer agent. The chain transfer agent controls the molecular weight of the polymer molecule by reacting with the propagating polymer radical to terminate its growth. It then causes the genesis of a new polymer chain thereby transferring the growth process from one discrete polymer molecule to another discrete polymer molecule. At least a part of the chain transfer agent is incorporated into the polymer molecule and is thus consumed in the process. The incorporated residue of the chain transfer agent can lead to undesirable end-groups on the polymer.

The chain transfer agents most commonly used are alkanethiols which possess an objectionable odour, lead to a wide distribution of molecular weights in batch polymerizations with certain monomers, do not allow the production of di-end functional polymers and have limitations as to the types of functional groups that can be installed at the end of the polymer chain. Additionally, the use of thiols causes the incorporation of a sulphur atom into the polymer chain and this can be a cause of premature discolouration of the polymer, which is especially deleterious in the coatings industry. There is also little scope with thiols for the chain transfer constant to be optimised for a particular polymerization. It is well known in the art that an unfavourable chain transfer constant can lead to a broad distribution of molecular weights in bath polymerizations. The optimum chain transfer constant in order to obtain narrow distributions of molecular weight in batch polymerizations take to moderate or high conversions is 1.0, as can be readily deducted from the article by T. Corner in *Advances in Polymer Science*, 62, 95 (1984).

International Patent Application PCT/AU87/00412 discloses novel chain transfer agents that help overcome many of the disadvantages of thiols and allow the installation of a number of different types of functional groups at the end of polymer molecules.

The present invention provides a process for the production of lower molecular weight polymers by free radical polymerization, which process is characterized by the addition of compounds of the general Formula I as chain transfer agents to an otherwise conventional polymerization system:

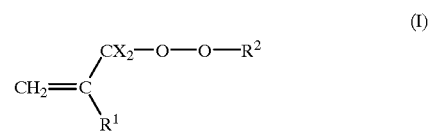

wherein $R^1$ is hydrogen, chlorine, an alkyl group, or a group capable of activating the vinylic carbon towards free radical addition;

$R^2$ is hydrogen, or an optionally substituted alkyl, alkenyl or aryl group or the group -CO—Z, where Z is $R^3$ or $OR^3$, where $R^3$ is hydrogen or optionally substituted alkyl, alkenyl or aryl group, X is a hydrogen atom, an alkyl or aryl group, or a halogen. The two X groups may be the same or different.

Preferably, $R^1$ is an optionally substituted phenyl or other aromatic group, or an alkoxycarbonyl or aryloxycarbonyl (—COOR), carboxy (—COOH), acyloxy (—O$_2$CR) carbamoyl (—CONR$_2$), or cyano (—CN) group.

Preferably, $R^2$ is a tertiary-butyl, cumyl or diphenylmethyl group, or a cyclohexyl or cyclopentyl group optionally substituted with an aryl or alkyl group.

The group X is preferably hydrogen.

As used herein the terms "optionally substituted" and "optional substituent" will be understood to imply the presence of any substituent group which does not undesirably or unfavourably affect the function of the compound of formula (I) in which it is present, that is to control the molecular weight of the polymer to be produced.

The optional substituents may therefore be chosen from a very wide range of known substituents, as will be evident to the person skilled in the art. By way of example only, substituents may be chosen from the following classes: ether, alkyl, ester, haloalkyl, halogen, aryl, hydroxy alkyl, nitrile.

At least one of the groups $R^1$ and $R^2$ may be or contain a reactive substituent, that is, one which is capable of undergoing a further chemical reaction subsequent to the polymerization reaction, whereby the polymer produced contains the said reactive group and is itself thereby capable of undergoing a further chemical reaction subsequent to the polymerization reaction.

Suitable reactive substituents include, for example, halogen, cyano, epoxy, hydroxy, amino, carboxy, alkoxycarbonyl, aryloxycarbonyl, carbamoyl, acyloxy, trialkylsilyloxy, trialkoxysilyl, phosphonate, allyl or alkenyl groups.

In the compounds of Formula I, substituted rings may have reactive substituent groups directly attached to the ring or indirectly attached by means of a methylene group or other side chain.

The process of this invention thus uses the compounds of general Formula I as alternatives to thiols or other chain transfer agents for the control of molecular weight. The compounds of Formula I may be added in pure form or mixed with diluents that allow safety and easier handling. The process of this invention may be operated in similar manner to conventional processes using thiols. The quantity of compound of Formula I required to give the desired molecular weight may be determined by the usual methods applicable to conventional chain transfer agents.

For example the process described herein is applicable to the manufacture of synthetic rubbers and other polymer formulations where reduced molecular weight aids processing and improves properties. The process can also be used to produce low molecular weight polymers and oligomers for a variety of applications such as high-solids surface coatings, paints, and adhesives. An added feature of the invention is that the low molecular weight polymers produced through application of the process contain epoxy groups at one end of the polymer chain. It is well known in the art that epoxy-containing polymers can react with other functional polymers such as those containing amine groups. Such reaction of epoxy-containing polymers can be used to prepare advanced polymer systems such as block or graft copolymers that have application, inter alia, as compatibilizing agents.

Compounds of general Formula I can be prepared from inexpensive starting materials. Unlike thiols, they do not possess an objectionable odour, nor do they incorporate any sulphur-containing groups that contribute to premature degradation or discolouring of the polymer. The compounds of Formula I display an unexpected high activity in controlling molecular weight in polymerization reactions and have chain transfer constants that are superior to those of thiols.

In most instances, their activity is such that their chain transfer constants approach the optimum of 1.0 for batch polymerizations and this activity is not as highly dependent as that of thiols on the type of the monomers used. Additionally, with this invention there is scope for the chain transfer constant to be tailored to a particular polymerization by the appropriate choice of the compound of Formula I and in particular by the appropriate choice of the substituent $R^1$.

Alkyl groups referred to in this specification may contain from 1 to 32 carbon atoms. Alkenyl and alkynyl groups may contain from 2 to 32 carbon atoms. Saturated, unsaturated, or aromatic carbocyclic rings may contain from 3 to 14 atoms.

Suitable cycloalkyl groups are cyclopentyl, cyclohexyl, cycloheptyl optionally substituted with aryl or alkyl groups. In all of the above aryl means an organic radical derived from an aromatic hydrocarbon by the removable of one hydrogen atom.

Australian Patent No. 586,285 (Akzo, N.V.) discloses peroxy ester compounds, similar to those of Formula I of the present invention, and their use as initiators of polymerization or for the curing of unsaturated polyester resins. There is no teaching or data in this patent on the effect of the claimed compounds on polymer molecular weight.

The present invention is based on the unexpected discovery that the compounds of Formula I offer efficient control of molecular weight in free radical polymerizations and act as chain transfer agents as opposed to initiators. The compounds of Formula I act in the manner expected of a conventional chain transfer agent in that the molecular weight of the product polymer is inversely proportional to the amount of compound added.

Apart from certain compounds disclosed in Australian Patent No. 586,285, the compounds of Formula I, wherein $R^1$ is other than hydrogen are novel, and form part of this invention.

The following are examples of preferred compounds of Formula I:

α-(t-butylperoxymethyl)styrene Ia,
α-(t-butylperoxymethyl)acrylonitrile Ib,
methyl α-(t-butylperoxymethyl)acrylate Ic,
ethyl α-(t-butylperoxymethyl)acrylate Id,
α-(cumeneperoxymethyl)styrene Ie,
i.e. compounds having the following formulae:

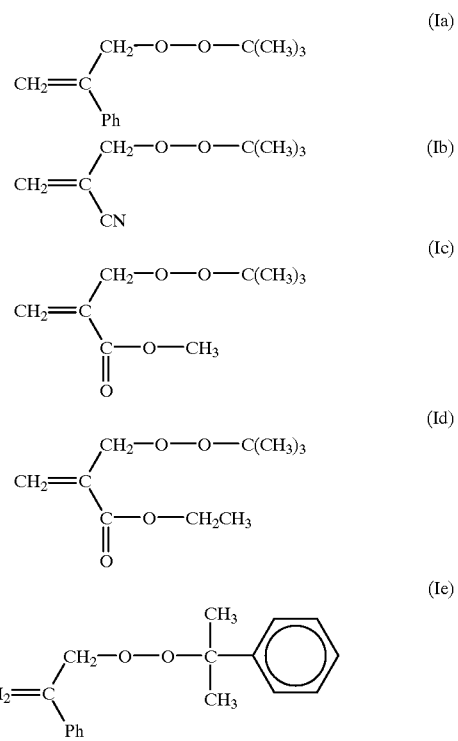

In contrast to the processes involving thiols, or the chain transfer agents described in the examples of International Patent Application PCT/AU87/00412, this process utilises agents with a different range of activities which do not contain sulphur, are more hydrolytically stable, and produce polymers which do not contain terminal unsaturation. A further unique feature of the process of this invention is that it directly and conveniently produces polymer chains that have a terminal epoxy group. As is well known in the art this terminal epoxy group can be utilized in crosslinking reactions to form networks by reaction with materials containing amine, hydroxyl, carboxylic acid or thiol groups. It is also possible to prepare block and graft copolymers by controlled reaction with polymers, oligomers and low molecular weight compounds containing the above functional groups.

The methods of production of the compounds of Formula I are illustrated by the following examples.

General Procedure for the Preparation of Compounds of Formula I

The preparation of α-(t-butylperoxymethyl)styrene (Ia) is illustrative of the general procedure.

α-(Bromomethyl)styrene (1.9 g) was added dropwise to a mixture of the sodium salt of tert-butylhydroperoxide (1.12 g) and dimethylformamide (5 ml) with cooling in an ice-salt bath. After the addition was complete, the mixture was left stirring for 4 hours at 21° C. and then it was poured into water and extracted three times with pentane. The combined extracts were dried over anhydrous magnesium sulphate and the solvent was removed to afford an oil (1.3 g) which was chromatographed on silica gel using 2% ethyl acetate/petroleum spirit as eluent to give pure Ia (499 mg). $^1$H NMR δ 1.23 (9H,s), 4.80 (2H,s), 5.35 (1H,s), 5.53 (1H,s), 7.1–7.6 (5H,m). Mass spectrum (NH$_3$) m/e 224 (MNH$_4^+$, 40%), 73 (100%).

α-(t-Butylperoxymethyl)acrylonitrile Ib was prepared similarly. $^1$H NMR (CDCl$_3$) δ 1.22 (9H,s), 4.49 (2H,s), 6.05 (1H,s), 6.09 (1H,s).

α-(Cumeneperoxymethyl)styrene Ie was prepared similarly with the sodium salt of cumene hydroperoxide. $^1$H NMR δ 1.53 (6H, s), 4.67 (2H,s), 5.20 (1H,s), 5.42 (1H,s), 6.9–7.5 (10H,m).

The acrylate derivatives Ic and Id were prepared as follows:

Methyl α-(t-Butylperoxymethyl)acrylate Ic

Methyl 1,3-dibromopropane-2-carboxylate (24.4 g) was added dropwise to a stirred solution of the sodium salt of tert-butylhydroperoxide (37 g) in dimethylsulfoxide (160 ml), while the temperature was maintained at 5° C. by cooling in an ice bath. The reaction mixture was further stirred for 2 h at 5° C. and then for 15 h at 18° C. After this time, it was poured into water and extracted with a mixture (1:1) of petroleum spirit (bp 30–40° C.) and ether. The extract was washed with water and dried over anhydrous magnesium sulphate and the solvent was removed by distillation to give the crude peroxide (8 g). This material was purified by careful distillation behind a safety screen to give Ic (bp 37–38° C./0.5 mmHg) (2.3 g) $^1$H NMR (CDCl$_3$) δ 1.22 (9H, s), 3.75 (3H,s), 4.64 (2H, s) 5.86 (1H, m), 6.33 (1H, s).

Ethyl α-(t-Butylperoxymethyl)acrylate Id was prepared similarly. $^1$H NMR (CDCl$_3$) δ 1.21 (9H, s), 1.30 (3H, t, J 7 Hz), 4.20 (2H, q, J 7 Hz), 4.63 (2H, s), 5.87 (1H, br s), 6.33 (1H, br s).

The following examples illustrate the use of the invention to produce polymers of controlled molecular weight and end group functionality.

EXAMPLE 1

Preparation of Low Molecular Weight Epoxide Terminated Polymers of Styrene using α-(t-Butylperoxymethyl)styrene Ia Azobisisobutyronitrile (34.9 mg) was dissolved in freshly distilled styrene (25 ml). Aliquots (5 ml) were removed and added to ampoules containing the amount of α-(t-butylperoxymethyl)styrene Ia shown below in Table 1. The mixtures were polymerised at 60° C. for 1 h in the absence of oxygen. The contents of the ampoule were then poured into methanol and the precipitated polymer was collected and dried in vacuo overnight. A small portion was examined by gel permeation chromatography (GPC) using a Waters Instrument connected to six μ-Styragel columns (10$^6$, 10$^5$, 10$^4$, 10$^3$, 500 and 100 Å pore size). Tetrahydrofuran was used as eluant at a flow rate of 1 ml/min and the system was calibrated using narrow distribution polystyrene standards (Waters).

TABLE 1

| Amount of Ia added (mg) | $\overline{M}_n$* |
|---|---|
| 0 | 93000 |
| 20.6 | 31000 |
| 41.8 | 20000 |

*Polystyrene-equivalent number average molecular weight, obtained by GPC.

The chain transfer constant ($C_x$), calculated from these data, was 0.89, which compares favourably with, say, that form n-butanethiol ($C_x$=0.66). These results show that the compound is an efficient chain transfer agent and that the process produced polymers of low molecular weight in a controlled manner. A sample of polystyrene produced similarly using 364 mg of the chain transfer agent Ia and 25 ml of the styrene/AIBN mixture was precipitated two further times from ethyl acetate/methanol to remove traces of the unreacted chain transfer agent. The resulting polymer of number average molecular weight 4 600 had a signal in the NMR spectrum at δ 3.2 ppm confirming the presence of the epoxy group. Estimation of the epoxy group by titration with pyridinium chloride/chloroform as described by Jungnickel et al in Organic Analysis, Vol 1, Interscience, New York 1953, p127 indicated that there was 0.8–1 epoxide group per polymer chain.

The following describes an experiment aimed at obtaining further evidence for the presence of a reactive epoxy group.

4-Methoxybenzyl mercaptan (0.92 g) was added to sodium hydride (0.12 g) in dry tetrahydrofuran (30 ml). The mixture was boiled under reflux for 4 h to ensure that no unreacted sodium hydride remained, after which time a solution of polystyrene (Mn=10200), produced with Ia, in tetrahydrofuran (20 ml) was added. The mixture was further boiled under reflux for 17 h and then cooled, poured into water and extracted with ethyl acetate. The extract was washed three times with water and dried (MgSO$_4$). The solvent was removed and the polymer was dried in vacuo. The dried polymer was then dissolve din ethyl acetate and precipitated twice with methanol as the non-solvent. After drying thoroughly, it was then examined by $^1$H NMR spectroscopy and showed signals at δ 3.6 and 3.7, from the benzyl and methoxy protons, respectively. These signals were different to those of the starting 4-methoxybenzyl mercapto group into the polymer, the most likely means of said incorporation being through reaction with the epoxy group of the polymer as is well known to the art. Hence, there is further confirmation of the presence of the epoxy end group.

EXAMPLE 2

Preparation of Low Molecular Weight Poly(methyl methacrylate) using α-(t-Butylperoxymethyl)styrene Ia Azobisisobutyronitrile (48.2 mg) was dissolved in freshly distilled methyl methacrylate (25 ml). Aliquots (2 ml) were removed and added to ampoules containing the amount of α-(t-butylperoxymethyl) styrene Ia shown below in Table 2. The mixtures were polymerised at 60° C. for 1 h in the absence of oxygen. The contents of the ampoule were then poured into hexane and the precipitated polymer was collected, dried, and examined as before.

TABLE 2

| Amount of Ia added (mg) | $\overline{M}_n$* |
|---|---|
| 0 | 149000 |
| 6.5 | 44400 |
| 19.7 | 18600 |

*Polystyrene-equivalent number average molecular weight, obtained by GPC.

The chain transfer constant ($C_x$), calculated form these data, was 0.83, which compared favourably with say, that from n-butanethiol ($C_x$=0.66). These results show that the compound is an efficient chain transfer agent and that the process produces polymers of low molecular weight in a controlled manner.

EXAMPLE 3

Preparation of Low Molecular Weight Poly(methyl acrylate) using α-(t-Butylperoxymethyl)styrene Ia Azobisisobutyronitrile (9.1 mg) was dissolved in freshly distilled methyl acrylate (25 ml). Aliquots (2 ml) were removed and added to ampoules containing thiophene-free benzene (8 ml) and the amounts of α-(t-butylperoxymethyl) styrene Ia shown below. The mixtures were polymerised at 60° C. for 1 h in the absence of oxygen. The volatiles were then removed and the polymers were dried in vacuo to constant weight and examined by GPC. Samples of poly (methyl acrylate) prepared in this manner using 0 mg, 13.7 mg, and 25.9 mg of α-(t-butylperoxymethyl)styrene Ia had number average molecular weights of 414000, 7600 and 4200, respectively. The chain transfer constant calculated from these data was 17.7. These results show that the compound is an efficient chain transfer agent and that the process produces polymers of low molecular weight in a controlled manner.

EXAMPLE 4
Preparation of Low Molecular Weight Poly(vinyl acetate) using α-(t-Butylperoxymethyl)styrene Ia Azobisisobutyronitrile (8.0 mg) was dissolved in freshly distilled vinyl acetate (50 ml). Aliquots (10 ml) were removed and added to ampoules containing the amounts of α-(t-butylperoxymethyl)styrene Ia shown below. The mixtures were polymerised at 60° C. for 1 h in the absence of oxygen. The volatiles were then removed and the polymers were dried in vacuo to constant weight and examined by GPC as described above. Samples of poly(methylacrylate) prepared in this manner using 0 mg, 5.1 mg, and 9.6 mg of α-(t-butylperoxymethyl)styrene Ia had number average molecular weights of 243 000, 14 800, 8 000, respectively. The chain transfer constant calculated form these data was 24. These results show the the compound is an efficient chain transfer agent and that the process produces polymers of low molecular weight in a controlled manner.

EXAMPLE 5
Preparation of Low Molecular Weight Polystyrene using α-(t-Butylperoxymethyl)acrylonitrile Ib Samples of polystyrene prepared in the manner of Example 1 using 0 mg, 20.7 mg, 39.0 mg, and 77.7 mg of α-(t-butylperoxymethyl)acrylonitrile Ib had number average molecular weights of 134 000, 10 200, 6 800, 4 700 respectively. The chain transfer constant calculated from these data was 2. These results show that α-(t-butylperoxymethyl)acrylonitrile Ib acts as an efficient chain transfer agent for styrene and that the process products polymers of low molecular weight.

EXAMPLE 6
Preparation of Low Molecular Weight Poly(methyl methacrylate) using α-(t-Butylperoxymethyl)acrylonitrile Ib Samples of poly(methylmethacrylate) prepared in the manner of Example 2 using 9.4 mg, 20 mg and 39 mg of α-(t-butylperoxymethyl)acrylonitrile Ib had number average molecular weights of 27 000, 14 000 and 8 100 respectively. The chain transfer constant calculated from these data was 0.85. These results show that α-(t-butylperoxymethyl) acrylonitrile Ib acts as an efficient chain transfer agent for methyl methacrylate and that the process produces polymers of low molecular weight.

EXAMPLE 7
Preparation of Low Molecular Weight Poly(methyl acrylate) using α-(t-Butylperoxymethyl)acrylonitrile Ib Samples of poly(methyl acrylate) prepared in the manner of Example 3 using 0 mg, 13.1 mg, 23.4 mg, 46.9 mg of α-(t-butylperoxymethyl)acrylonitrile Ib had number average molecular weights of 673 000, 25 700, 15 000, and 8 500, respectively. The chain transfer constant calculated from these data was 0.73. These results show that α-(t-butylperoxymethyl)acrylonitrile Ib acts as an efficient chain transfer agent for methyl acrylate and that the process produces polymers of low molecular weight.

EXAMPLE 8
Preparation of Low Molecular Weight Poly(vinyl acetate) using α-(t-Butylperoxymethyl)acrylonitrile Ib Samples of poly(methyl methacrylate) prepared in the manner of Example 4 using 0 mg, 5.0 mg, and 11.3 mg of α-(t-butylperoxymethyl)acrylonitrile Ib had number average molecular weights of 540 000, 3 700, and 1 450, respectively. The chain transfer constant calculated from these data was 90. These results show that α-t-butylperoxymethyl) acrylonitrile Ib acts as a very active chain transfer agent for vinyl acetate and that the process produces polymers of low molecular weight.

EXAMPLE 9
Preparation of Low Molecular Weight Polystyrene using methyl α-(t-Butylperoxymethyl)acrylate Ic Samples of polystyrene prepared in the manner of Example 1 using 0 mg, 21.2 mg, 41.1 mg, and 80.7 mg of methyl α-(t-butylperoxymethyl)acrylate Ic had number average molecular weights of 134 000, 22 900, 11 500, and 6 800, respectively. The chain transfer constant calculated from these data was 1.64. These results show that methyl α-t-butylperoxymethyl)acrylate Ic acts as an efficient chain transfer agent for styrene and that the process produces polymers of low molecular weight.

EXAMPLE 10
Preparation of Low Molecular Weight Poly(methyl methacrylate) using Methyl α-(t-Butylperoxymethyl) acrylate Ic Samples of poly(methyl methacrylate) prepared in the manner of Example 2 using 0 mg, 11.7 mg, 20.8 mg, and 39.5 mg of methyl α-(t-butylperoxymethyl)acrylate Ic had number average molecular weights of 364 000, 45 200, 27 900, and 15 200, respectively. The chain transfer constant calculated from these data was 0.63. These results show that methyl α-(t-butylperoxymethyl)acrylate Ic acts as a useful chain transfer agent for methyl methacrylate and that the process produces polymers of lower molecular weight.

EXAMPLE 11
Preparation of Low Molecular Weight Poly(methyl acrylate) using Methyl α-t-Butylperoxymethyl)acrylate Ic Samples of poly(methyl acrylate) prepared in the manner of Example 3 using 0 mg, 15.4 mg, 25.6 mg, and 50.3 mg of methyl α-(t-butylperoxymethyl)acrylate Ic had number average molecular weights of 937 000, 23 200, 13 600, and 7 500, respectively. The chain transfer constant calculated from these data was 1.02. These results show that methyl α-(t-Butylperoxymethyl)acrylate Ic acts as an efficient chain transfer agent for methyl acrylate and that the process produces polymers of low molecular weight.

EXAMPLE 12
Preparation of Low Molecular Weight Poly(vinyl acetate) using Methyl α-(t-Butylperoxymethyl)acrylate Ic Samples of poly(vinyl acetate) prepared in the manner of Example 1 using 0 mg, 6.0 mg, 10.7 mg, and 18.5 mg of methyl α-(t-Butylperoxymethyl)acrylate Ic had number average molecular weights of 291 000, 15 000, 4 300, and 1 800, respectively. The chain transfer constant calculated from these data was 45. These results show that methyl α-t-Butylperoxymethyl)acrylate Ic acts as a very active chain transfer agent for vinyl acetate.

EXAMPLE 13
Preparation of Low Molecular Weight Poly(methyl methacrylate) with α-(Cumeneperoxymethyl)styrene Ie AIBN (48.3 mg) was dissolved in freshly distilled methyl methacrylate (25 ml). Aliquots (5 ml) were removed and added to ampoules containing 0 mg, 16.6 mg, and 35.3 mg of α-(cumeneperoxymethyl)styrene Ie. The mixtures were polymerized at 60 C. for 1 h in the absence of oxygen. The contents of the ampoules were then precipitated in hexane and dried in vacuo to afford polymers of molecular weights 555000 (673 mg), 47900 (297 mg), and 26000 (129 mg), respectively. The chain transfer constant calculated from these data is 0.8, showing that the process using α-(cumeneperoxymethyl)styrene Ie produces polymers of low molecular weight. The chain transfer constant of 1.0, is ideal for obtaining low distributions of molecular weight in bulk polymerizations at medium to high conversions.

EXAMPLE 14
Preparation of Low Molecular Weight Polystyrene with α-(Cumeneperoxymethyl)styrene Ie AIBN (34.9 mg) was dissolved in freshly distilled styrene (25 ml). aliquots (5 ml) were removed and added to ampoules containing 0 mg, 29.4 mg, and 52.3 mg of α-(cumeneperoxymethyl)styrene Ie. The mixtures were polymerized at 60 C. for 2 h in the absence of oxygen. The contents of the ampoules were then precipitated in methanol and dried in vacuo to afford polymers of molecular weights 89300 (160 mg), 32700 (139 mg), and 22700 (170 mg), respectively. The chain transfer constant calculated from these data is 0.8, showing that the process using α-(cumeneperoxymethyl)styrene Ie produces polymers of low molecular weight. The chain transfer constant of 0.8 shows that the process with Ie is efficient in reducing molecular weight.

The claims defining the invention are as follows:

1. A compound having a formula (I):

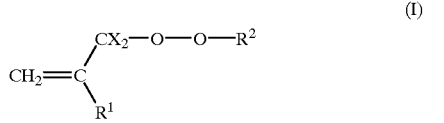

(I)

wherein $R^1$ is a radical selected from the group consisting of

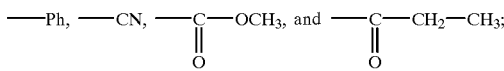

$R^2$ is hydrogen;

and X is hydrogen.

2. A compound having a formula (I):

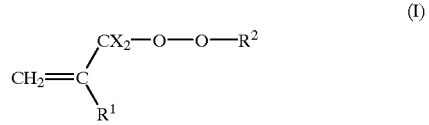

(I)

wherein $R^1$ is —Ph;

$R^2$ is hydrogen;

and X is an alkyl group or a hydrogen atom, and the two X groups may be the same or different.

3. A compound according to claim 1 wherein $R^1$ is —Ph.

4. A compound as claimed in claim 1 wherein $R^1$ is —CN.

5. A compound as claimed in claim 1 wherein $R^1$ is

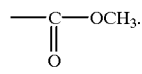

6. A compound as claimed in claim 1 wherein $R^1$ is

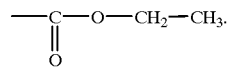

* * * * *